United States Patent [19]

Lawrence

[11] 4,087,440
[45] May 2, 1978

[54] N-(HYDROCARBYL THIOPHOSPHORYLDITHIO)-IMIDE VULCANIZATION AGENTS AND ACCELERATORS

[75] Inventor: John P. Lawrence, Stow, Ohio

[73] Assignee: The Goodyear Tire & Rubber Company, Akron, Ohio

[21] Appl. No.: 587,933

[22] Filed: Jun. 18, 1975

[51] Int. Cl.² .......................................... C07D 207/48
[52] U.S. Cl. ............................ 260/326 S; 260/45.8 N; 260/79.5 C; 260/79.5 P; 260/784; 260/800
[58] Field of Search ..................... 260/79.5 C, 79.5 P, 260/784, 800, 326 S, 45.8 N

[56] References Cited

U.S. PATENT DOCUMENTS

| | | | |
|---|---|---|---|
| 2,891,059 | 6/1959 | Malz et al. | 260/293.63 |
| 2,995,568 | 8/1961 | Malz et al. | 260/326 E |
| 3,044,981 | 7/1962 | Malz et al. | 260/326 E |
| 3,544,531 | 12/1970 | Morita | 260/784 |
| 3,586,696 | 6/1971 | Kerwood et al. | 260/326 S |
| 3,642,727 | 2/1972 | Ashworth et al. | 260/79.5 C |
| 3,709,907 | 1/1973 | Behforouz | 260/326 S |
| 3,865,781 | 8/1973 | Lohr | 260/79.5 B |

Primary Examiner—V. P. Hoke
Attorney, Agent, or Firm—J. A. Rozmajzl

[57] ABSTRACT

N-(hydrocarbyl thiophosphoryldithio)-imides such as N-(O,O-diisopropyl thiophosphoryldithio)-phthalimide are used as accelerators with, or as a partial or total replacement for, the elemental sulfur used in conventional sulfur vulcanization systems for diene rubbers.

3 Claims, No Drawings

N-(HYDROCARBYL THIOPHOSPHORYLDITHIO)-IMIDE VULCANIZATION AGENTS AND ACCELERATORS

This invention relates to imide compounds which can be used as accelerators along with elemental sulfur in the vulcanization of diene rubbers, or as partial or total replacements for the elemental sulfur in such systems. It also relates to the use of the imides as activators when used with other accelerators. More particularly it relates to a method of preparing a vulcanizate with improved heat aged properties.

The use of elemental sulfur in the vulcanization of diene rubbers is commonly accompanied by the use of one or more organic accelerators whose purpose it is to increase the rate of vulcanization. These accelerators, however, will sometimes result in prevulcanization (scorching) of the unvulcanized rubber.

The heat aged resistance of vulcanized rubbers has been achieved in the past by using a large amount of a vulcanization accelerator such as a sulfenamide in combination with a low level of elemental sulfur. Such systems, however, typically give rise to significantly reduced vulcanization rates. Good heat aged resistance and increased vulcanization rates are obtained by alternatively using compounds such as tetramethylthiuram disulfide in the absence of elemental sulfur. Unvulcanized rubbers compounded with the latter system, however, have an increased tendency to prematurely vulcanize.

It is desirable that new organic accelerators be found which will have a reduced tendency to prevulcanize. It is also desirable that a system be found which will provide vulcanized rubbers having a high resistance to heat aged degradation. Such a system should also provide a rapid vulcanization rate, while possessing a limited tendency to prematurely vulcanize the rubber.

It is also desirable that new compounds be found which will increase the rate of vulcanization without adversely affecting processing safety (scorch).

It is an object of the present invention to provide novel accelerators to be used in combination with elemental sulfur in the sulfur vulcanization of diene rubbers. It is also an object of the present invention to provide organic accelerators which have a reduced tendency to vulcanize the rubber prematurely. It is still another object of the present invention to provide a sulfur vulcanization system which will result in a vulcanizate having resistance to heat degradation, which can be vulcanized at a relatively rapid rate and with a reduced tendency to prematurely vulcanize the rubber. Another object is to provide a method to produce vulcanizates. Other objects will become apparent as the description proceeds.

The objects of the present invention are accomplished by using an accelerator in a diene rubber in combination with elemental sulfur or as a total or partial replacement for elemental sulfur in a sulfur vulcanization system, an imide having the following structural formula

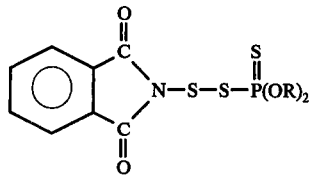

wherein R is selected from the group consisting of alkyl radicals (straight chain or branched) having 1 to 12 carbon carbon atoms, cycloalkyl radicals having 5 to 6 carbon atoms in the ring, said cycloalkyl radicals being unsubstituted or monosubstituted with an alkyl radical containing 1 to 4 carbon atoms and aryl radicals having 6 to 10 carbon atoms in the aromatic ring, said aryl radicals being unsubstituted or substituted with one or two (preferably one) substituents selected from the group consisting of alkyl radicals having 1 to 4 carbon atoms, alkoxy radicals having 1 to 4 carbon atoms and the chloro radical.

Preferably R is selected from the group consisting of ethyl, n-propyl, isopropyl, n-butyl, isobutyl, sec-butyl, n-hexyl, n-octyl, and cyclohexyl.

The following list of compounds is intended to illustrate, but not to limit, the imides of the present invention.

N-(O,O-dimethyl thiophosphoryldithio)-phthalimide
N-(O,O-diethyl thiophosphoryldithio)-phthalimide
N-(O,O-di-n-propyl thiophosphoryldithio)-phthalimide
N-(O,O-di-isopropyl thiophosphoryldithio)-phthalimide
N-(O,O-di-n-butyl thiophosphoryldithio)-phthalimide
N-(O,O-di-sec-butyl thiophosphoryldithio)-phthalimide
N-(O,O-di-isobutyl thiophosphoryldithio)-phthalimide
N-(O,O-di-n-hexyl thiophosphoryldithio)-phthalimide
N-(O,O-di-n-octyl thiophosphoryldithio)-phthalimide
N-(O,O-di-n-dodecyl thiophosphoryldithio)-phthalimide
N-(O,O-dicyclohexyl thiophosphoryldithio)-phthalimide
N-(O,O-diphenyl thiophosphoryldithio)-phthalimide
N-(O,O-di-p-tolyl thiophosphoryldithio)-phthalimide
N-(O,O-di-p-chlorophenyl thiophosphoryldithio)-phthalimide The performance of the compounds of the present invention as vulcanization agents is not dependent upon their method of preparation.

The imides can be prepared in the following general fashion.

Equimolar quantities of N,N'-thiobis(phthalimide) and the appropriate dithiophosphoric acid are mixed in a hydrocarbon solvent such as benzene or toluene. The mixture is stirred and refluxed until the precipitation of phthalimide is complete, then cooled to room temperature and filtered to remove the insoluble phthalimide by-product. The filtrate is concentrated to remove the solvent, leaving the product.

The course of the reaction may be depicted as shown below.

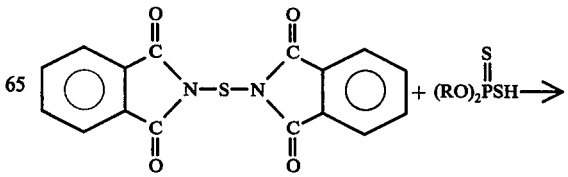

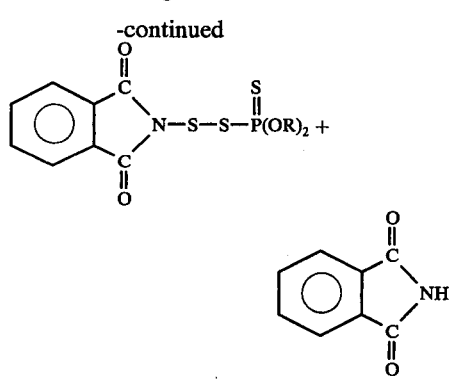

Although equimolar amounts of the reactants are preferred, the molar ratio of the N,N'-thiobis(phthalimide) to dithiophosphoric acid may vary from 1:1 to 5:1 without affecting the outcome of the reaction. The excess of N,N'-thiobis(phthalimide) is readily separated from the product due to its high degree of insolubility in the reaction solvent. The use of ratios less than 1:1, that is, an excess of dithiophosphoric acid over N,N'-thiobis(phthalimide), will still provide the desired product, however, it will be accompanied by the formation of an undesirable by-product, a bis(O,O-dihydrocarbyl thiophosphoryl)-trisulfide. The temperature of the reaction can vary from 25° C. to 150° C. but is preferably from 50° C. to 120° C. The choice of solvent for the reaction is not critical for the performance of the preparative process. As solvents one may use aliphatic or aromatic hydrocarbons such as hexane, heptane benzene, toluene or xylene, alcohols such as methanol, ethanol and 2-propanol, ethers such as diethylether, tetrahydrofuran or dioxane, and halogenated solvents such as chloroform, carbon tetrachloride or chlorobenzene. It is most advantageous, however, to select a solvent in which the N-(O,O-dihydrocarbyl thiophosphoryldithio)-phthalimides are soluble and the phthalimide by-product insoluble to allow separation of the two products. For this reason, hydrocarbon solvents such as benzene, toluene, or xylene are preferred. No catalysts are required for the successful operation of the process. The reaction may also be carried out at, above, or below atmospheric pressure although there is no advantage to carrying out the reaction at other than atmospheric pressure. None of the above information is intended to be limiting, but merely to be used as guidelines.

The imides of the present invention are extremely versatile compounds. They are sulfur donors and can be used to replace a part or all of the sulfur in a vulcanization system where improved resistance to high temperature thermal degradation is desired. They can be used as the sole accelerator with a conventional level of sulfur to increase the vulcanization rate and state of vulcanization. Where another accelerator is being used with sulfur, such as sulfenamides, thiazoles, etc., some of the imides can be used as activators to increase the vulcanization rate. Overall they can be used to provide balanced processing and vulcanization characteristics as well as vulcanizates with good physical properties and resistance to high temperature degradation.

When used as sulfur donors to improve the heat resistance of vulcanizates, the amounts of the imide and elemental sulfur to be used will vary depending upon the presence of other accelerators and the balance of physical properties required in the vulcanized rubber. Generally the amount of imide to be used should be at least half of the amount of sulfur replaced and may amount to up to twice the amount of sulfur replaced. As the amount of sulfur removed increases, the quantity of imide with which it is replaced should be increased to an even greater extent to maintain physical properties. Generally incremental replacement of sulfur with imide leads to improved retention of aged physical properties and a decreased tendency toward premature vulcanization. The vulcanization rate may either be increased or decreased slightly depending upon the amounts of sulfur and imide employed.

The sulfur donors of this invention function most effectively when used in the presence of a conventional sulfur vulcanization accelerator. Examples of such accelerators are aromatic thiazole accelerators which include N-cyclohexyl-2-benzothiazolesulfenamide, 2-mercaptobenzothiazole, N-tert.butyl-2-benzothiazole sulfenamide, 2-benzothiazolyl diethyldithiocarbamate and 2-(morpholinothio)-benzothiazole. Other thiazole accelerators which may be used include 2-(aminodithio)-thiazoles and 2-(aminotrithio)-thiazoles such as 2-(morpholinodithio)-benzothiazole. Amine salts of mercaptobenzothiazoles, for example, the tertbutylamine salt of mercaptobenzothiazole, and like salts of morpholine and 2,6-dimethylmorpholine can be used.

The amount of the imide to be used and the amount of sulfur, if any, to be used therewith, depends to a large degree upon the nature of the vulcanization system in which it is to be used, the polymer to be vulcanized and the processing, vulcanization and vulcanizate characteristics which are desired.

Generally when used as a total or partial replacement for sulfur, the amount of imide can vary from 0.5 part to 5.0 parts, the sulfur level varying from zero to 2.0 parts and the total amount of sulfur plus imide ranging from 1.5 to 5 parts.

When used as primary vulcanization accelerators, the compounds of this invention can be used in a range from 1 to 10 parts by weight per 100 parts by weight of rubber, preferably from 1.5 to 5 parts, together with elemental sulfur in an amount from 1 to 5 parts, preferably 2 to 4 parts.

The above remarks as to amounts are not intended to be limitations as to the practice of the present invention, but rather as guidelines which may be used.

The imides of the invention can be used in any sulfur vulcanizable rubber including natural and synthetic rubbers and mixtures thereof. Synthetic rubbers that can be improved by the process of this invention include homopolymers and copolymers of dienes, both conjugated and non-conjugated, e.g., 1,3-dienes such as 1,4-butadiene and isoprene. Examples of such synthetic rubbers include neoprene (polychloroprene), cis-1,4 polybutadiene, cis-1,4 polyisoprene, butyl rubber, copolymers of 1,3-butadiene or isoprene with monomers such as styrene, acrylonitrile and methyl methacrylate. Ethylene/propylene terpolymers, for example ethylene/propylene/dicyclopentadiene terpolymers, also benefit from the practice of the present invention.

The imides can be added to the rubbers by an conventional technique such as milling or Banburying and can be used with conventional compounding ingredients such as carbon black and zinc oxide.

All of the working examples herein are intended to illustrate but not limit the scope of the present invention. Unless indicated otherwise, all parts are parts by weight.

The following examples, 1 and 2, illustrate the preparation of various imides of the present invention.

EXAMPLE 1

N-(O,O-diisopropyl thiophosphoryldithio)-phthalimide

A 5 liter, 3-neck flask equipped with a mechanical stirrer and reflux condenser is charged with 162 grams (0.5 mole) of N,N'-thiobis(phthalimide), 2500 milliliters of benzene, and 107 grams (0.5 mole) of O,O-diisopropyl dithiophosphoric acid. The mixture is stirred and refluxed 1.5 hours. After cooling to room temperature the mixture is filtered to remove phthalimide and the filtrate is concentrated in vacuo. The residue is recrystallized from 2 liters of heptane to yield 170 grams (87%) N-(O,O-diisopropyl thiophosphoryldithio)-phthalimide. The melting point was 105° C. to 107° C. An elemental analysis of the product was run to confirm the structure. The theoretical values for $C_{14}H_{18}NO_4PS_3$ are C, 42.97; H, 4.60; N, 3.58; P, 7.93; S, 24.55. The actual values wee C, 42.96; H, 4.73; N, 3.74; P, 7.71, S, 24.68.

EXAMPLE 2

N-(O,O-dicyclohexyl thiophosphoryldithio)-phthalimide

A 500 milliliter round bottom flask fitted with a magnetic stirring bar was charged with 19.5 grams (0.06 mole) of N,N'-thiobis(phthalimide) and 300 milliliters of benzene. The mixture was stirred and 17.6 grams (0.06 mole) of O,O-dicyclohexyl dithiophosphoric acid was added gradually from an addition funnel. The addition funnel was replaced with a reflux condenser and the mixture refluxed one hour, then cooled and filtered to remove phthalimide. The filtrate was concentrated in vacuo and the residue recrystallized from a mixture of methanol and benzene (1:1) to afford 15.6 grams (55%) of N-(O,O-dicyclohexyl thiophosphoryldithio)-phthalimide. The melting point was 83° C. to 85° C. An elemental analysis of the product was run to confirm the structure. The theoretical values for $C_{20}H_{26}NO_4PS_3$ are C, 50.96; H, 5.52; N, 2.97; P, 6.58; S, 20.38. The actual values were C, 51.01; H, 5.50; N, 2.96; P, 6.50; S, 20.92.

The other compounds included within the practice of the present invention can be prepared by using the same or similar techniques as described in the preceding working examples. Synthetic routes to these compounds are not limited, however, to these particular reactions and procedures.

The following examples illustrate the use of various imides of the present invention as sulfur replacements or primary vulcanization accelerators or activators. Mooney Scorch tests were performed using the large rotor as described in ASTM D 1646-61. A recorder was employed to continuously plot viscosity versus time. The number of minutes required for the viscosity curve to rise five points above the minimum was taken as a measure of scorch inhibition. Larger values indicate a greater resistance to scorch or premature vulcanization.

Data on vulcanizing characteristics were obtained with a Monsanto Oscillating Disc Rheometer, as described by Decker, Wise, and Guerry in Rubber World, page 68, December 1962. Pertinent data from this instrument are: $t_4$, the minutes required for the Rheometer torque curve to rise four units above the minimum torque value, and $t_{90}$, the minutes required for the torque curve to reach 90 percent of the difference between the maximum and minimum torque values.

The $t_{90}$ value is considered to be the time required to reach the optimum vulcanized state. The difference, $(t_{90} - t_4)$ is indicative of the time necessary for actual vulcanization to take place after the scorch delay period has ended, i.e., is a relative measure of vulcanization rate.

$\Delta Rh$ is the difference between the maximum and minimum torque obtained on the rheometer curve. It is used as a measure of the degree (state) of vulcanization.

Compression set tests were conducted in accordance with ASTM D-395 which measures the residual decrease in thickness of rubber and rubberlike elastomers after compression.

Examples 3 and 4 illustrate the use of various levels and type of N-(hydrocarbyl thiophosphoryldithio)-imides of the present invention as sulfur replacements. All of the compounds evaluated (Mix Numbers 2 to 5) demonstrate a significant improvement in the resistance of the rubber stocks to heat degradation (note percent retention of tensile and elongation) when compared to the control (Mix Number 1). Compression set was also substantially decreased when part or all of the sulfur was replaced with the compounds of this invention. Some of the compounds provide a greater resistance to premature vulcanization. Some of the compounds also decreased the vulcanization time.

EXAMPLE 3

Natural rubber formulations of the following composition were mixed on a mill and vulcanized at 135° C. The vulcanized rubbers were aged in a circulating air oven at 100° C. and the tensile strength and elongation at break of the aged rubbers determined.

| Mix Number | 1 | 2 | 3 | 4 | 5 |
|---|---|---|---|---|---|
| Smoked sheets | 100 | 100 | 100 | 100 | 100 |
| H.A.F. carbon black | 50 | 50 | 50 | 50 | 50 |
| Stearic acid | 3 | 3 | 3 | 3 | 3 |
| Softener | 3 | 3 | 3 | 3 | 3 |
| Zinc oxide | 3 | 3 | 3 | 3 | 3 |
| Amine antioxidant | 1 | 1 | 1 | 1 | 1 |
| Sulfur | 2.5 | 1.5 | 1 | 0.5 | — |
| N-cyclohexylbenzothiazole-sulfenamide | | | | | |
| N-(O,O-diisopropyl thiophosphoryl-dithio)-phthalimide | — | 0.6 | 1.2 | 1.8 | 2.4 |
| Mooney Scorch at 132° C. (mins. to minimum + 5 value) | 7.2 | 8.5 | 8.8 | 9.3 | 12.5 |
| Vulcanization Time at 135° C. (mins.) | 30 | 30 | 30 | 35 | 50 |
| Tensile strength (Kg/cm$^2$) | 273 | 298 | 286 | 277 | 257 |
| Elongation at break (percent) | 460 | 520 | 500 | 520 | 575 |
| Modulus at 300% elongation (Kg/cm$^2$) | 175 | 165 | 165 | 147 | 108 |
| Oven aging at 100° C. 3 days | | | | | |

-continued

| Mix Number | 1 | 2 | 3 | 4 | 5 |
|---|---|---|---|---|---|
| Tensile strength (Kg/cm$^2$) | 159 | 196 | 202 | 206 | 183 |
| Percent retained | 58 | 66 | 71 | 74 | 71 |
| Elongation (percent) | 220 | 320 | 350 | 420 | 500 |
| Percent retained | 48 | 62 | 70 | 81 | 87 |
| 6 days | | | | | |
| Tensile strength (Kg/cm$^2$) | 75 | 131 | 145 | 173 | 141 |
| Percent retained | 27 | 44 | 51 | 62 | 55 |
| Elongation (percent) | 125 | 225 | 260 | 360 | 440 |
| Percent retained | 27 | 43 | 52 | 69 | 77 |
| Compression set at 70° C/22hrs. | | | | | |
| 25% compression (percent) | 26 | 20 | 18 | 16 | 16 |

EXAMPLE 4

Natural rubber formulations of the following composition were mixed on a mill and vulcanized at 135° C. The vulcanized rubbers were aged in a circulating air oven at 100° C. and the tensile strength and elongation at break of the aged rubbers determined.

| Mix Number | 1 | 2 | 3 | 4 | 5 |
|---|---|---|---|---|---|
| Smoked sheets | 100 | 100 | 100 | 100 | 100 |
| H.A.G. carbon black | 50 | 50 | 50 | 50 | 50 |
| Stearic acid | 3 | 3 | 3 | 3 | 3 |
| Softener | 3 | 3 | 3 | 3 | 3 |
| Zinc oxide | 3 | 3 | 3 | 3 | 3 |
| Amine antioxidant | 1 | 1 | 1 | 1 | 1 |
| Sulfur | 2.5 | 1 | 1 | 1 | 1 |
| N-cyclohexylbenzothiazole sulfenamide | 1 | 1 | 1 | 1 | 1 |
| N-(O,O-dimethyl thiophosphoryl-dithio)-phthalimide | — | 1.2 | — | — | — |
| N-(O,O-diethyl thiophosphoryl-dithio)-phthalimide | — | — | 1.2 | — | — |
| N-(O,O-diphenyl thiophosphoryl-dithio)-phthalimide | — | — | — | 1.2 | — |
| N-(O,O-dicyclohexyl thiophosphoryl-dithio)-phthalimide | — | — | — | — | 1.2 |
| Mooney Scorch at 132° C. (mins. to minimum + 5 value) | 7.9 | 5.8 | 7.3 | 5.9 | 10.0 |
| Vulcanization Time at 135° C. (mins) | 30 | 25 | 30 | 30 | 25 |
| Tensile strength (Kg/cm$^2$) | 287 | 295 | 284 | 226 | 282 |
| Elongation at break (percent) | 460 | 565 | 475 | 410 | 510 |
| Modulus at 300% elongation (Kg/cm$^2$) | 187 | 144 | 170 | 158 | 164 |
| Oven aging at 100° C. | | | | | |
| 3 days | | | | | |
| Tensile strength (Kg/cm$^2$) | 147 | 220 | 219 | 160 | 208 |
| Percent retained | 51 | 75 | 77 | 71 | 74 |
| Elongation (percent) | 220 | 440 | 370 | 290 | 370 |
| Percent retained | 48 | 78 | 78 | 71 | 73 |
| 6 days | | | | | |
| Tensile strength (Kg/cm$^2$) | 78 | 120 | 138 | 96 | 126 |
| Percent retained | 27 | 41 | 49 | 42 | 45 |
| Elongation (percent) | 130 | 290 | 260 | 205 | 260 |
| Percent retained | 28 | 51 | 55 | 50 | 51 |
| Compression set at 70° C/22 hrs. | | | | | |
| 25% compression (percent) | 27 | 24 | 16 | 19 | 18 |

EXAMPLE 5

Example 5 illustrates the use of various N-(hydrocarbyl thiophosphoryldithio)-imides as primary vulcanization accelerators. All of the compounds tested demonstrate the ability to accelerate the sulfur vulcanization of rubber. An unexpectedly low state of vulcanization was reached with mix 2. Mixes 1, 3, and 5 demonstrate a good balance between the state of cure, the rate of cure, and protection against premature vulcanization.

Natural rubber formulations of the following composition were mixed on a mill and vulcanized at 135° C. Mooney scorch and rheometer data were gathered on the compounded stocks.

| Mix Number | 1 | 2 | 3 | 4 | 5 |
|---|---|---|---|---|---|
| Smoked sheets | 100 | 100 | 100 | 100 | 100 |
| H.A.F. carbon black | 50 | 50 | 50 | 50 | 50 |
| Stearic acid | 3 | 3 | 3 | 3 | 3 |
| Softener | 3 | 3 | 3 | 3 | 3 |
| Zinc oxide | 3 | 3 | 3 | 3 | 3 |
| Amine antioxidant | 1 | 1 | 1 | 1 | 1 |
| Sulfur | 2.5 | 2.5 | 2.5 | 2.5 | 2.5 |
| N-(O,O-diisopropyl thiophosphoryl-dithio)-phthalimide | 2 | — | — | — | — |
| N-(O,O-dimethyl thiophosphoryl-dithio)-phthalimide | — | 2.5 | — | — | — |
| N-(O,O-diethyl thiophosphoryl-dithio)-phthalimide | — | — | 2.5 | — | — |
| N-(O,O-diphenyl thiophosphoryl-dithio)-phthalimide | — | — | — | 2.5 | — |
| N-(O,O-dicyclohexyl thiophosphoryl- | | | | | |

| Mix Number | 1 | 2 | 3 | 4 | 5 |
|---|---|---|---|---|---|
| dithio)-phthalimide | — | — | — | — | 2.5 |
| Rheometer torque, ΔRh | 63.9 | 37.9 | 66.7 | 55.6 | 61.1 |
| Rheometer scorch at 135° C.,$t_4$(mins) | 17.2 | 8.9 | 16.3 | 10.0 | 18.4 |
| Optimum vulcanization time, $t_{90}$(mins) | 47.9 | 22.2 | 49.7 | 55.0 | 50.7 |
| Vulcanization rate, $t_{90}$-$t_4$ (mins.) | 30.7 | 13.3 | 33.4 | 45.0 | 32.3 |
| Tensile strength (Kg/cm$^2$) | 255 | 223 | 257 | 187 | 254 |
| Elongation at break (percent) | 510 | 610 | 490 | 400 | 510 |
| Modulus at 300% elongation (Kg/cm$^2$) | 142 | 79 | 147 | 132 | 141 |
| Shore A hardness | 63 | 54 | 64 | 61 | 63 |

As noted in the results under Example 5, all of the compounds tested acted as accelerators when used in combination with elemental sulfur. Had no accelerator been used, the vulcanization rate values would have been in the hundreds.

In the presence of other accelerators these compounds act as non-scorching (note Mooney and Rheometer scorch in Example 6) activators (see $t_{90}-t_4$).

Example 6

| Mix Number | 1 | 2 | 3 |
|---|---|---|---|
| N.R. Base Stock as in Example 5 | 162.5 | 162.5 | 162.5 |
| N-morpholinothiobenzothiazole | 0.5 | 0.5 | 0.5 |
| N-(O,O-diisopropyl thiophosphoryl-dithio)-phthalimide | — | 0.5 | 1.0 |
| Mooney scorch at 132° C. (mins. to minimum + 5 value) | 10.9 | 10.2 | 9.1 |
| Rheometer scorch at 135° C., $t_2$ (mins.) | 14.0 | 12.8 | 12.3 |
| Rheometer torque, ΔRh | 61.3 | 68.7 | 74.9 |
| Optimum vulcanization time, $t_{90}$ (mins.) | 56.0 | 37.0 | 34.0 |
| Vulcanization rate, $t_{90}$-$t_4$ (mins.) | 38.6 | 21.7 | 19.3 |
| Tensile strength (Kg/cm$^2$) | 287 | 287 | 263 |
| Elongation at break (percent) | 530 | 505 | 420 |
| Modulus at 300% elongation(Kg/cm$^2$) | 148 | 163 | 188 |
| Shore A hardness | 63 | 67 | 68 |

Addition of N-(O,O-diisopropyl thiophosphoryldithio)-phthalimide results in a significant increase in vulcanization rate with a corresponding decrease in vulcanization time with only a very slight sacrifice in scorch. Tensile and elongation are essentially unchanged, but modulus and hardness are increased.

The above examples are not intended to be limiting, but rather illustrative. Any of the sulfur donors, accelerators and rubbers described earlier herein can be substituted in the preceding examples. In addition, the levels of the sulfur donors, accelerators, and other components in said examples could be altered in accordance with the general teachings herein.

The method of incorporating the imides into the rubber is not critical, any of the conventional techniques such as milling and Banburying being satisfactory.

While certain representative embodiments and details have been shown for the purpose of illustrating the invention, it will be apparent to those skilled in this art that various changes and modifications may be made therein without departing from the spirit or scope of the invention.

What is claimed is:

1. A process of preparing an imide having the following structural formula

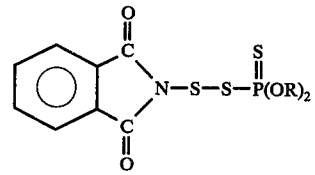

wherein R is selected from the group consisting of alkyl radicals having 1 to 12 carbon atoms, cycloalkyl radicals having 5 to 6 carbon atoms in the ring, said cycloalkyl radicals being unsubstituted or monosubstituted with an alkyl radical containing 1 to 4 carbon atoms and aryl radicals having 6 to 10 carbon atoms in the aromatic ring, said aryl radicals being unsubstituted or substituted with one or two substituents selected from the group consisting of alkyl radicals having 1 to 4 carbon atoms, alkoxy radicals having 1 to 4 carbon atoms and the chloro radical comprising reacting N,N'-thiobis(phthalimide) having the structure

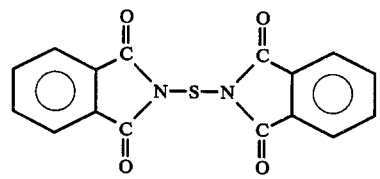

with dithiophosphoric acid having the structure

wherein the molar ratio of the phthalimide to the acid is from 1:1 to 5:1 and the reaction temperature is from 25° C. to 150° C.

2. The process of claim 1 wherein R is selected from the group consisting of ethyl, n-propyl, isopropyl, n-butyl, isobutyl, sec-butyl, n-hexyl, n-octyl, and cyclohexyl.

3. The process of claim 1 wherein the imide is N-(O,O-diisopropyl thiophosphoryldithio)-phthalimide.

* * * * *